United States Patent [19]

Weaver et al.

[11] Patent Number: 4,732,680

[45] Date of Patent: Mar. 22, 1988

[54] BIOCHEMICAL CONVERSION PROCESSES

[75] Inventors: Timothy W. Weaver, Golden, Colo.; Patric L. Friend; Wilson K. Whitekettle, both of Conroe, Tex.

[73] Assignee: Betz Laboratories, Inc., Trevose, Pa.

[21] Appl. No.: 732,023

[22] Filed: May 8, 1985

[51] Int. Cl.$^4$ .................................................. C02F 3/34
[52] U.S. Cl. ..................................... 210/610; 210/631; 210/908; 210/909
[58] Field of Search ............... 210/601, 610, 611, 631, 210/908, 909, 632

[56] References Cited

U.S. PATENT DOCUMENTS

| | | | |
|---|---|---|---|
| 4,169,049 | 9/1979 | Salkinoja-Salonen | 210/611 X |
| 4,179,365 | 12/1979 | Sumi | 210/610 |
| 4,352,886 | 10/1982 | Pillis et al. | 210/601 X |
| 4,420,397 | 12/1983 | Kaneko et al. | 210/611 |
| 4,485,016 | 11/1984 | Hopkins | 210/632 |
| 4,493,895 | 1/1985 | Coloruotolo et al. | 210/611 X |
| 4,535,061 | 8/1985 | Chakrabarty et al. | 210/601 X |
| 4,664,805 | 5/1987 | Focht | 210/611 |

FOREIGN PATENT DOCUMENTS 1058899A 12/1980 U.S.S.R.

OTHER PUBLICATIONS

"Regulation of Phenol Degradation in *Pseudomonas putida*", Janke et al., Zeitschrift fur Allegemune Mikrobiologie, vol. 21, 1981, pp. 295-303.

"Bacterial Degradation of Diphenylmethane, a DDT Model Substrate", Appl. Microbiology, 20:608-611, 1970, Focht et al.

Chem. Abstracts, 98-95100t, 1983.

Primary Examiner—Tom Wyse
Attorney, Agent, or Firm—Alexander D. Ricci

[57] ABSTRACT

The present invention is directed to a method of chemical addition to a microbial population to condition the population to (i) enhance bioconversion or biodegradation of a given substrate, or (ii) survive and perform greater bioconversion of a substrate when the population is exposed to fluctuating and in particular shock loads of the substrate. The method comprises conditioning the population by exposure of such to a non-toxic or non-inhibitory amount of a material which is biochemically or structurally similar to the substrate in question. The method is applicable in systems where the production of useful metabolites is the objective, as well as in waste treatment where degradation of a waste into more acceptable form is to be achieved.

14 Claims, 7 Drawing Figures

BIOCHEMICAL CONVERSION PROCESSES

BACKGROUND OF THE INVENTION

The present invention is directed to any system or systems where microbial populations are specifically utilized for a given purpose. The invention has as its objective the enhancement of these systems to achieve the purpose or purposes with greater efficacy and with minimization of some of the side problems experienced prior to the advent of the present invention.

Bioconversion is a process wherein living organisms are employed to carry out a physical and/or chemical change in a substance. The substance can be natural or man-made. The bioconversion processes to which the present invention is directed include both synthetic and degradative processes. Examples of bioconversion processes include, but are not limited to, fermentations, wastewater treatment, biopolymer production, biomining, and microbially-enhanced oil recovery. Fermentations in this context are defined as the process of microbial production of useful products which are primary or secondary metabolites of microbial origin, such as antibiotics, ethanol, acetone, glycols, organic acids, amino acids, vitamins, antimetabolites, esters, ethers, ketones, aldehydes, flavorings, foods, hormones, enzymes, lipids, alkaloids, surfactants, and gases such as methane. The microbial production process may be either aerobic or anaerobic.

Wastewater treatment is defined as the process by which microbial populations are used to remove and degrade waste substances or a particular chemical or chemicals, generated either by industrial activity or by municipalities, contained in an aqueous environment. This can be achieved by aerobic systems, such as trickling filters, and activated sludge systems, or anaerobic treatment systems.

Biopolymer production is the conversion of substrates by a microbial population to homopolymers or heteropolymers having desired properties. Biomining is the extraction and concentration of mineral elements from ores and rocks, mediated by microorganisms.

Microbial enhanced oil recovery is the process of freeing oil deposits trapped in geologic formations, both subterranean and surface, through the action of microorganisms deliberately introduced into the geologic formation. The microorganisms employed are selected for their ability to reduce the viscosity of the trapped oil, to increase dramatically the pressure in the formation, or to bring about other desired changes to aid in forcing out the trapped oil.

As indicated above, the use of microbial consumption of a substrate(s) for various purposes has been widespread. Because of the technical and commercial success of these applications, whether for waste water treatment or for the production of metabolites through fermentation and the like procedures, the respective industries are continually researching and developing different techniques, microbial populations, substrates, etc. in an attempt to further enhance these applications from both effectiveness and economic points of view.

Such is the case with the present inventors, who have discovered a means of increasing the overall effectiveness of microbial populations' consumption and/or bioconversion of an organic substrate (e.g. toxic chemical), without an attendant increase or decrease in (i) the microbial population itself, and (ii) solid waste production (including but not limited to both sludge and biomass).

With respect to waste water treatment, the process objective is to remove as much waste, or a particular constituent thereof, as possible from the water being treated while producing the least amount of biomass or sludge and/or the most complete elimination as possible of the particular substrate.

Likewise, with the production of metabolites (useful chemicals), it is desirable to achieve as close to total consumption or bioconversion of the substrate as possible, as quickly as possible, with the use of smaller microbial populations (i.e., have energies expended for bioconversion rather than in the reproduction of additional cells) in order to positively affect the economies of the production process.

It is common in systems as described above for a good portion of the cell's energies to be expended in the production of new microbial cells which, if not successful in competing for survival with the other cells, die and thus add to the biomass that must be disposed. More specifically, one can view cellular activities in terms of "bio-economics". In order to obtain maximal proliferation, or at the least subsistence, a cell must maximize its efficiencies so that there is insurance of a niche for its continuing activities.

To maximize its efficiencies, all activities of the cell are intercontrolled and intercommunication is carried out on the molecular level.

Maximum efficiency is selected for daily by competition from other species and environmental pressures. If activities are not optimized the price the species must pay is extinction.

As earlier indicated, in biological waste treatment the process objective is to remove as much waste or a given pollutant from the polluted influent as possible while producing the least amount of biomass or sludge for final disposal. It is believed that the present inventors have discovered a means for accomplishing this as well as enhancing fermentation systems to increase the rate of the process, e.g., the rate of ethanol production from glucose, without the need for high capital expenditures or expensive efforts.

While the present invention has applicability in any process wherein a substrate (chemical) and a microbial population are utilized at appropriate conditions to either produce a desired end product or to change the substrate or chemical to another form, perhaps a more desirable form, the invention will be discussed comprehensively as it pertains to waste treatment. More specifically the invention will be discussed as it pertains and applies to the biodegradation of a specific species of chemical pollutant to reduce the concentration of the pollutant in the waste stream, eliminate or alter the pollutant to a more acceptable, dischargeable form. As is well known, many if not most chemicals are subject to dischargeable limitation by the regulations promulgated by federal, state and sometimes municipal authorities. Accordingly, industrial as well as municipal waste management teams are constantly looking for ways of producing acceptable effluent discharges, in order to comply with the regulations, and, it is hoped, doing so in an economical manner. The present invention is meant to aid in achieving these goals.

Technology - Waste Treatment

The most commonly used secondary waste treatment operation for the disposal of industrial organic wastes is the activated sludge process. The process ideally converts carbon-containing pollutants to $CO_2$ plus microbial cellular by-products. The cells are then separated, the $CO_2$ evolves and the process effluent can be safely released to a receiving stream or reused as needed. The success of this disposal process is contingent on a steady state operation which allows stable physiological conditions for the growth of the biomass. Deviations from this steady state operation have direct influence on the performance of the microbial community responsible for wastewater cleanup, and therefore on the process effluent quality. Because of the intermittent nature of industrial processes, operational perturbations are the norm in industrial wastewater treatment operations. The amplitude and character of these perturbations are a critical factor in the daily operation, and long-term survival, of a biological wastewater treatment process. These, in turn, also have a direct influence upon the frequency of regulatory encounters experienced by a particular industry.

Transients in biological waste treatment performance stem from operational and influent changes which create genetic, physiological or ecological alterations in the system's microbial community. Microbial adaptation has the potential to minimize the transient's impact, but this requires a lag period before full system performance is restored.

Influent character variations which can contribute to the transient behavior of steady-state operation frequently come in as a shock load to the system. Variability in the temperature, flow rates, pH, and quality and/or quantity of both organic and inorganic constituents of the wastewater can be of such a magnitude that the biomass cannot cope, and system obliteration can occur. Without a viable biomass to catalyze the necessary biodegradative reactions, the waste components merely flow through the system. Not only does regulatory non-compliance result but system startup (or reseed) becomes a problem.

Amelioration or prevention of shock loading effects has typically been attempted by physical measures, i.e., through the use of equalization basins to dampen a transient's impact. This capital-intensive cure is reasonable for most shock loads, but is not necessarily effective for qualitative organic shock loading, which is exposure to an organic substrate that is potentially biodegradable but can be toxic to the biomass.

The present inventors reasoned that if a state of adaptation could be achieved and maintained for an infrequent but potentially detrimental substrate, the effects of qualitative shock loading might be minimized or avoided. It was postulated that a state of adaptation could be maintained by presenting the bacterial population with a molecule which would be structurally analogous to the problem substrate it might see. This adaptation was envisioned to be physiological, rather than a change in the population's structure. Thus, the biodegradative capacity of the population would be enhanced.

A compound will be biodegradable only when microbes are present which have an enzymatic system capable of degrading the compound. The compound usually has value to the microbes as a source of energy or as a resource for biosynthesis. The successful exploitation of these compounds for energy production and biosynthesis, as well as the survival of a species, is linked to a well-run cellular economy. As earlier indicated if energy is spent foolishly by a cell the species cannot survive. This well-run economy is linked to several metabolic phenomena.

Microbial metabolism must be carefully controlled by the organisms, because the many enzymatic reactions that are occurring to yield energy and build new biomass are simultaneous. The enzymatic reactions are controlled by two general mechanisms, control of enzyme synthesis and control of activity of enzymes after they are synthesized. Enzyme activity is controlled by soluble, low molecular weight compounds which interact with the enzyme and speed up or slow down the rate at which a substrate is turned over. Among the types of compounds which can affect the rates of the reactions are products of the enzymatic reactions, either immediate reaction products of a given enzyme or end reaction products of a series of enzymes.

Enzyme synthesis is controlled by mechanisms known as induction and repression. Induction promotes the formation of an enzyme, or a group of enzymes that make up a metabolic pathway, and repression inhibits the formation of an enzyme or group of enzymes. Induction and repression are also controlled by soluble, low molecular weight compounds. These compounds interact directly or indirectly with the genetic information of the cell and control the expression of the genes by influencing which genes will be turned on and which will be turned off. The types of compounds which act as inducers or repressors include, respectively, the substrates upon which the enzymes will act or the products which the enzymes will form.

The rationale of having an inducer or repressor control the formation of an enzyme or system of enzymes can be derived in purely energetic terms. It is wasteful to carry around enzymes used to degrade a compound which is not present, or to synthesize a compound present in excess, because it takes a great deal of cellular energy and biosynthetic precursors to form these unneeded enzymes. It is much more efficient to have a mechanism which allows the formation of the necessary enzymes only when they are needed or useful.

The process of adaptation of a microbial population to any environmental change can be interpreted, in large measure, in terms of controlling metabolic responses. When adaptation can occur by turning on a pathway to degrade a compound, the population has an opportunity to enhance its survival by using the compound for growth. If the compound being degraded is toxic, and degradation detoxifies it, survival of the population is further enhanced.

A disadvantage of such adaptation schemes, however, is manifest if a population is unable to adapt rapidly enough to a potentially toxic material. In such an instance, a toxic concentration may be reached and the race will be lost. Under these circumstances, having an increased level of adaptation, which would be inefficient in terms of energy expenditure, would have long-term survival value and thus be beneficial to the population. The inventors concluded that a compound in the pollutant chemical or waste degradation pathway would induce the formation of degradative enzymes and prevent shock loading effects.

In order to demonstrate whether this phenomenon would occur, experiments were conducted first in the laboratory, then with model reactors at a waste treatment site, and then finally in an operating waste treatment system. The results of the respective studies conducted and tests performed established that there was considerable merit in the inventor's reasoning and conclusions.

DRAWINGS

The Figures of the Drawings will be described in association with the actual examples to which they are relevant.

DESCRIPTION OF THE INVENTION

The inventors basically discovered a method which is adaptable to bioconversion processes (production of useful metabolites) as well as biodegradation of wastes, pollutants and the like to produce more acceptable, less toxic and perhaps more dischargeable products, from a regulatory standpoint.

The invention is directed to a method for enhancing and improving the rate and amount of bioconversion of a chemical (or waste) contained in an aqueous medium by a suitable microbial population. The process generally comprises treating an aqueous mixture of the particular microbial population utilized for the conversion at appropriate conditions and time period with an effective amount for the purpose of a second chemical. The second chemical is one which may be bioconverted by said population, which is sterically, structurally, or biochemically analogous to said chemical, which is not toxic to the microbial population at the dosages used. The use of the second chemical, because of its analogous structure to the first chemical, permits the microbial population to adapt to the first chemical thereby affecting the population in such a manner that its bioconversion capacity for said chemical is increased without a substantial attendant increase in population.

The microbial population may be treated with the second chemical prior to, concurrently with or after its contact with said first chemical.

Preferably the microbial population is treated with the second chemical prior to its contact with the first chemical. This permits a more efficient method of removing the chemical or waste, and at the same time protects the microbes in the event of fluctuation, and in particular unexpected increases (shocks), of the undesired chemical in the aqueous system containing the chemical. However, substantial enhancement of bioconversion of the chemical or waste occurs when treatment with the second chemical is simultaneous with, or even after, an exposure of the microbial population to the chemical or waste.

The concentration of the second chemical, or perhaps more specifically called the "analogous compound," used to adapt the microorganisms must be sufficient to permit substantial bioconversion of the chemical or waste which would otherwise not occur. The concentration of the second chemical necessary for enhancement will usually be less than the concentration of the chemical to be bioconverted, and the concentration of the second chemical used will be below the inhibitory or toxic concentration of the second chemical. While the second chemical may itself be converted or assimilated by the microbial population, it is not mandatory that conversion or assimilation of the second chemical occur. As discussed earlier the concentration of chemical being subjected to bioconversion fluctuates and therefore the amount of the second chemical (analogous compound) utilized to adapt the microbial population should be varied accordingly. While the inventors do not wish to be limited to the mechanisms believed to take place during the adaptation stage, it is thought that the bioconversion capacity of the microbial population is enhanced because the analogous compound stimulates the production of a greater supply of enzyme(s) in the microbes of the population, which enzyme(s) is responsible for the bioconversion of the chemical, either directly, or through the process of cometabolism.

From the foregoing, it is apparent that the term "bioconversion" is being utilized in a generic sense and is intended to encompass those applications where useful metabolites are produced, e.g. fermentation process, as well as the degradation of toxic, undesired, pollutants that may be contained in an industrial or municipal waste treatment system.

From the studies conducted and considering the pollutant chemical species utilized, it would be expected that the invention would be applicable for the removal of most pollutants such as the toxic aromatic organic compounds and in particular those structurally related to the species tested, i.e. the phenolic pollutants. In order to utilize the inventive method for the purpose it would be necessary to determine, and perhaps evaluate, the analogous compound which would be most suitable for a given pollutant (waste).

With respect to the pollutant species studied, i.e. phenol, the analogous compound utilized, which in the dosages used were not toxic to the microbes providing the degradation, was benzoic acid, having the structure Of course, as with any analogous compound, it would be expected that the water soluble salts, e.g. Na, K, $NH_4$ and the like would be equally utilized while the benzoic acid was found to be quite effective in the adaptation of microbes for the biodegradation of phenols. It is expected that other derivatives of benzoic acid would also be quite effective for use in phenol or phenolic pollutant removal. Postulated for use would be the following benzoic acid forms and derivatives:

| Halogenated benzoic acids | Catechol |
| Hydroxy benzoic acids | Amino benzoic acids |
| Alkyl benzoic acids | |

The term "analog" and "analogous compound" as used herein is intended to mean that the chemical has certain likenesses, sterically, structurally, or biochemically, to the species of the chemical or waste to be subjected to conversion, but the analog is not the same as the chemical or waste. In this regard the invention is different for example, from the invention described in Russian Patent 19 SU(11)1058899A, where the microbes are adapted, prior to their use, by the use of the chemicals which are ultimately to be biodegraded.

Obviously in order for the bioconversion to take place, the microbial population must be one (although perhaps a mixed population as normally found in waste treatment systems) which is capable, under the conditions of exposure to the substrate, of performing the bioconversion. In operating systems for waste treatment, the microbes necessary for the biodegradation of a given species of pollutant/chemical generally are present if that system has been exposed to the pollutant and has been used to degrade such to some degree.

Usage levels of the analog as regards the level of microbial population, as would be expected, are dependent upon the microbial population (pure or mixed), the substrate (and pollutant) and the particular analog. In some instances the analog may be quite effective at certain dosages in stimulating the population used; however, at much higher dosages, the analog could be toxic to the population, or inhibit the desired and bioconversion without toxic effects. Accordingly the factor needs to be taken into consideration, in those instances where it is applicable, to assure the use of non-toxic dosages. Minor experimentation would be required to determine the proper dosages.

Generally speaking the dosage rates could be in the range of 5 ppm to 500 ppm, and most preferably in the range of 5 ppm to 100 ppm, based upon the amount appropriate for the microbial population.

The present method permits exposure of microbes prior to or concurrently with exposure of the pollutant chemical. The differences are significant since as can be concluded for the results set forth later herein, treatment of microbial population with the analog after a shock exposure of population to a toxic species, led, it is believed, to the recovery of the population.

The following represents the postulated analogs for the degradation of the neutral chemical compounds.

| Compound to be Subjected to Bioconversion | Possible Analogs |
| --- | --- |
| 1. Toluene, benzene, phenol, ethylbenzene, etc. | 1. Benzoate, catechol, benzyl alcohol, mandelic acid, salicylic acid or salts, etc. |
| 2. Nitrobenzene, nitrophenols etc. | 2. Aniline |
| 3. Naphthalene, phthalate esters, phenanthrene, etc. | 3. Salicylic acid, solegenin, catechol, etc. |
| 4. 2, 3, 7, 8 tetrachloro-benzo-p-dioxin, etc. | 4. 2, 3, 7, 8 tetrahydroxy dibenzo-p-dioxin |
| 5. DDT | |

-continued

| Compound to be Subjected to Bioconversion | Possible Analogs |
| --- | --- |

EXPERIMENTAL

Laboratory

In order to establish whether the instant invention would function in accordance with the original concept, experiments were conducted in a laboratory model. The substrate chosen for study, phenol, is a common "problem" influent component found in the waste waters of petroleum refineries, plastics manufacturers, coal gasification plants, coke producers, pulp and paper mills and chemical manufacturers. Problems caused by phenol shock loading of biological waste treatment operations are known to include deterioration of effluent quality, in that both phenol and Chemical Oxygen Demand (COD) effluent levels increase, and biomass destruction due to phenol toxicity.

The inventors believed that benzoate and catechol, because they were known intermediate breakdown products of phenol, would act as analogs of phenol and enhance phenol degradation. However, studies published by D. Janke, R. Pohl, and W. Fritoche[1] showed that benzoate inhibited phenol degradation in static batch cultures, and catechol had no effect on the rate of phenol degradation. The work of D. D. Focht, R. S. Horvath, and M. Alexander showed that the presence of benzoate could enhance the amount of cyclic compound degraded in non-aqueous soil batch test systems. The work in static batch tests reported by these workers is irrelevant to practical bioprocessing operations.

[1]D. Janke, R. Pohl and W. Fritsche, 1981, Regulation of phenol degradation in *Pseudomonas putida*. Zeitschrift fur Allegemune Mikrobiologie, Volume 21, pp. 295-303.

Demonstration of biodegradability of cyclic molecules has traditionally been done by three approaches: (1) the determination of the ability of some common prototrophic microorganisms to grow at the expense of the organic material of interest; (2) "die-away" tests employing relatively rapid spectrophotometric methods to follow disappearance of UV absorbance caused by molecular cleavage; and (3) the elective culture method in which those organisms capable of utilizing the compound of interest should increase in number during an enrichment period. No work of this sort, however, has ever been applied to continuous culture or bioprocessing operations.

In the study conducted, the main concern was not only documentation of biodegradation, but also enhancement of specific compound removal efficiencies in a continuous flow system. Because of this, an improved "die-away" evaluation of system performance was necessary. Components used in this evaluation were (1)

high resolution gas capillary chromatography as an analytical measurement of specific substrate alteration and quantitative variation, and (2) a mixed microbial population with the known potential to degrade the specific substrate of interest (phenol), in addition to degrading a wide range of other carbon sources. When coupled with a highly controlled testing environment (the chemostat test system utilized) a refined "die-away" system was available.

Equipment Used for Laboratory Studies

The bioreactor used in the study was the model C-32 chemostat (New Brunswick Scientific, Edison, N.J.). The configuration was developed as a bio-oxidation model.

Reactor pH control was achieved with Model 5997-10 Horizon pH controllers and Ingold type 465-35-K-9 probes (Ingold Electrode, Andover. Mass.). The acid demand for pH adjustment was provided by automatic addition of sterile 2N HCl, via peristaltic pumps, specific heads and viton tubing.

Sterile Nutrient Broth (BBL, Cockeysville, Md.) at ½ strength was used as the primary organic substrate and was contained in a primary influent reservoir.

Solutions of the potential analogs sodium benzoate and catechol and mixtures thereof were pumped in as secondary influent component's with pumps, specific heads and silicon tubing. Analogs were combined with phenol, the secondary substrate and shocking compound, in a separate influent reservoir.

Bioreactor seed was obtained from an industrial system where the activated sludge treatment system was used for phenol degradation. The seed had been ultra-frozen in 10% glycerol and stored at −85° C. in individual cryogenic vials with 1.5 mL seed per vial, and was quick-thawed as needed. Once thawed, the vial contents were taken up in 10 mL of ½ strength Nutrient Broth and vortexed. Five mL of this suspension were used as initial batch inoculum for each chemostat.

Once inoculated, chemostats were allowed to run 3 days in the batch mode before continuous culture was begun. Batch and continuous operating parameters were as follows: pH—7.0; agitation speed—500 rpm; aeration—1.0 slpm; and temperature 28° to 29° C.

Reactors were run in continuous flow for a time sufficient to achieve five volume turnovers to reach steady state. The dilution rate was 0.015 hr⁻, at which rate the reactor turnover time was about 67 hours. Substrate feed was split into two components, 0.25 mL/min for primary substrate (Nutrient Broth) and 0.10 mL/min for the secondary substrate (phenol with/without analog). The total influent flow was thus 0.35 mL/min. The volume of the reactor contents was fixed at 1400 mL.

Several dosages of sodium benzoate, catechol, or sodium benzoate/catechol mixtures were tested for effects on bioreactor phenol utilization. Since the secondary substrate flow was 28.6% of the total influent flow (0.10 mL/min., ÷0.35 mL/min), the concentration of secondary substrate in the secondary substrate reservoir was (1÷0.2857) or 3.5 times the desired concentration in the reactor vessel. For example, to achieve a concentration of 25 ppm of sodium benzoate in the reactor, the secondary substrate reservoir contained 87.5 ppm of benzoate. After benzoate flow to the reactor had begun, the concentration of benzoate in the reactor increased linearly until it reached the theoretical concentration. The time required to reach the theoretical concentration was one reactor turnover time, or about 67 hr. Effects of reactor conditioning with the analogs prior to phenol shocking were analyzed, as well as were the effects of analog addition at the time of phenol shock inception, and addition during shock progression.

Phenol shocking was conducted by initiating phenol feed from the secondary reservoir at time zero. Phenol concentrations stated in the results are the theoretical concentrations fed into the reactors, and these reached their maximum and steady-state levels after one reactor turnover time.

Determination of reactor performance enhancement was made by comparison of phenol breakthrough and COD removal data from the control reactor with data from reactors receiving analog or analog combinations at various times prior to or during phenol shocking. Analyses were performed on the reactor effluents, which were theoretically samples of the contents of a well-mixed reactor.

Phenol analysis was performed by gas chromatographic analysis on a Hewlett-Packard Model 5880A gas chromatograph. Columns used were 30 meter×0.25 mm×0.25 u film thickness fused silica capillary column and a 12 m×0.2 mm×standard thickness fused silica capillary column.

Reactor samples (10 mL) for gas chromatographic (G.C.) analysis were acidified with 4 drops of 6N HCl. These were then extracted sequentially by shaking with 3 mL, 2 mL and 2mL of methylene chloride (HPLC grade) and the extracts were centrifuged @ 15,000 rpm between extractions to break the emulsion and separate the layers. The methylene chloride extracts were combined and a 2 µl sample was used for G.C. analysis. The aqueous layer was discarded. The following instrument operating parameters were used for analysis:

| | |
|---|---|
| 1. | injection-manual, splitless |
| 2. | calibration - external standard |
| 3. | Oven temperature profile: |
| | Initial value = 30 C. |
| | Initial time = 3.00 min. |
| | Level 1 |
| | program rate = 30 C./min |
| | final value = 90 C. |
| | final time = 0.00 min |
| | Level 2 |
| | program rate = 10 C./min |
| | final value = 150 C. |
| | final time = 0.00 min. |
| | Post run value = 225 C. |
| | Post time = 3.00 min. |
| 4. | detector used - flame ionization |
| 5. | detector temperature = 200 C. |
| 6. | injector temperature = 250 C. |
| 7. | gas flow @ split vent = 16.4 ml/min |
| | carrier = 17.0 psi (helium), makeup gas = 13 psi |
| | Linear velocity through column = 39.3 cm/sec. |
| | purge activation time = 0.30 minutes |

Reactor samples for chemical oxygen demand (COD) analysis were centrifuged @ 10,000× for 10 minutes and the supernatant was analyzed for determination of soluble COD components. Analysis for COD was by the Hach low level (0–150 mg/L) and high level (0–1500 mg/L) spectrophotometric methods (Hach Chemical, Loveland, Co.). Spectrophotometric readings were made with a Bausch and Lomb Spectronic 20 (@ 420 nm for low level or 620 nm high level) or a DR100 Hach COD Colorimeter.

Experimentation into the response of a mixed population in the continuously stirred tank reactor (CSTR) to phenol shock loading was centered around operation of the test population in a steady state while being exposed to the phenol analogs sodium benzoate and catechol, and mixtures thereof. After steady state was reached, the phenol content of the reactor influent was stepped up until phenol breakthrough was achieved in the control reactor. "Die off" of this phenol breakthrough was followed and control (unexposed) and analogdosed reactor operating data were compared.

Results of Laboratory Studies

The expected response of this experimentation was that the control reactor would respond in a classical manner to shock loading, i.e., phenol levels in the effluent would rise due to the inability of the reactor population to degrade phenol. The effluent phenol levels would either peak out after biomass adaptation occurred and return to baseline, or reach the influent phenol concentration. Washout of the biomass would then occur due to phenol toxicity. It was expected that simultaneously with these events effluent and reactor COD levels would rise during the shock load and follow the same profile as the phenol levels, although at a slightly higher level, reflecting inhibition of non-phenolic substrate breakdown as well. On the other hand, it was expected that analog exposure would dampen or eliminate these classic effects which usually occur during shock loading, because the analog would allow the population to preadapt and be better able to degrade the phenol.

Figure 1:
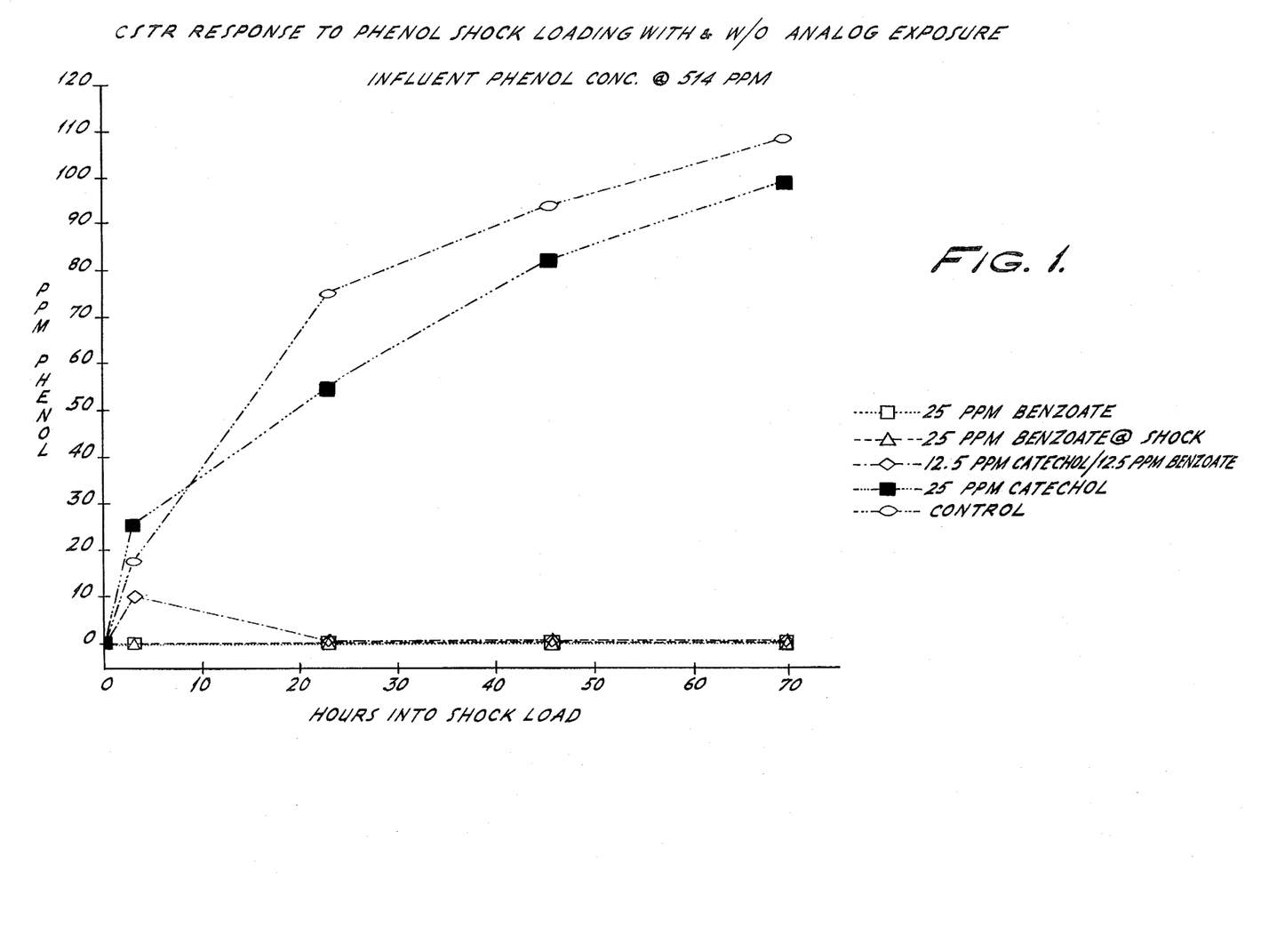
Figure 2:
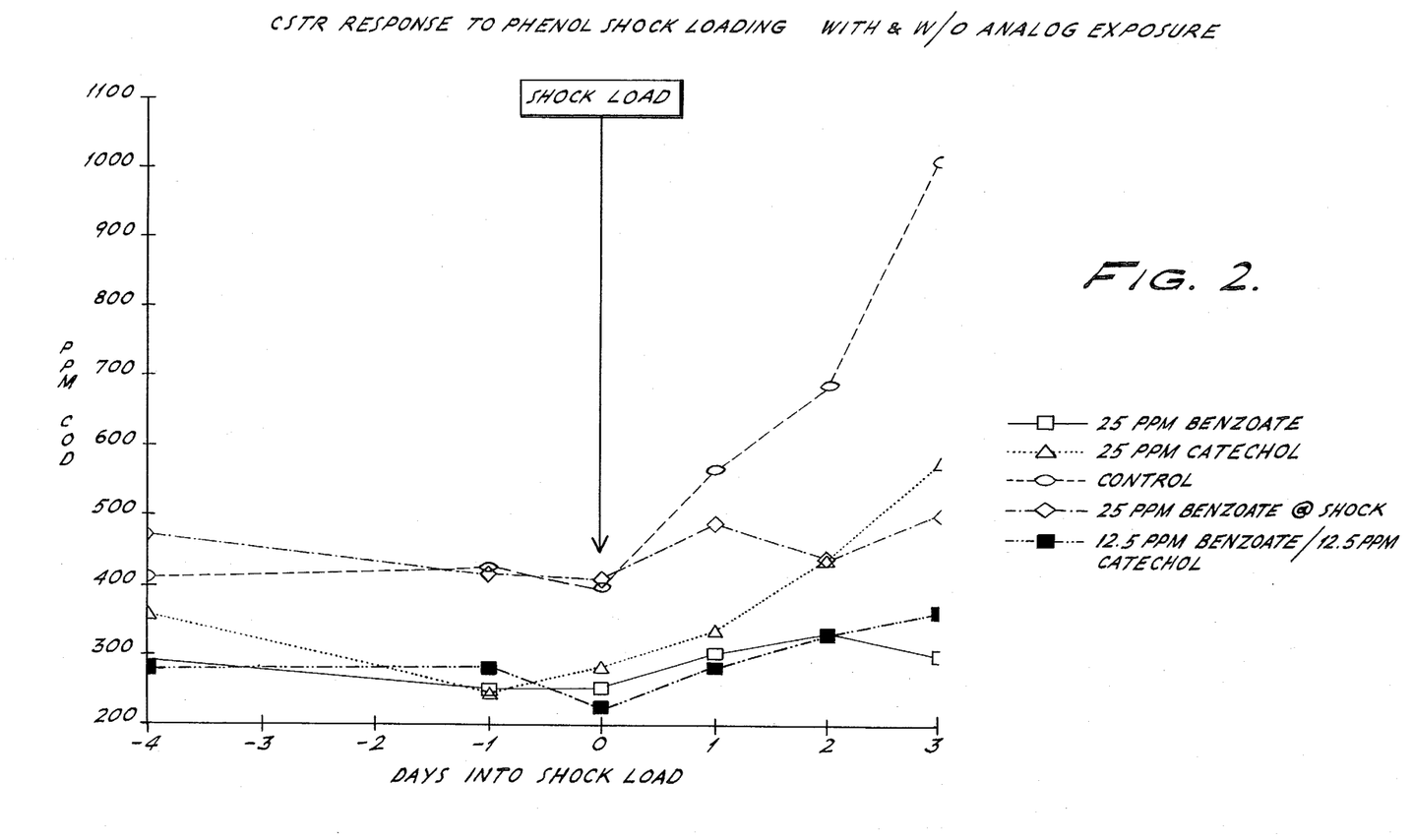

FIGS. 1 and 2 and Tables 1 and 2 represent COD and phenol analyses of the contents of bioreactors treated in the following manner and shocked with 514 ppm of phenol:
A. continuous feed of 25 ppm benzoate before and during phenol shock loading;
B. 25 ppm benzoate fed continuously after the beginning of phenol shock load;
C. continuous feed of 12.5 ppm benzoate and 12.5 ppm catechol before and during the phenol shock;
D. continuous feed of 25 ppm catechol before and during phenol shock loading;
E. control reactor receiving no analog. All other reactor operating parameters were the same.

The control reactor showed a "classical" shock load response, in that the phenol level of the reactor rose dramatically over three days and COD removal was disturbed. Sampling was not carried out long enough to determine whether or not phenol and COD levels returned to baseline. However, the toxic effects of a phenol breakthrough are evident. If the assumption is made that one ppm of phenol has a COD of three ppm (as can be shown theoretically), then the increase in COD level can be attributed to the increased phenol in the effluent.

The results from the reactors treated with benzoate were markedly different. No phenol appeared in the effluent of the treated reactors, regardless of whether the benzoate was fed prior to or concurrently with the phenol shock. COD removal remained the same in the benzoate-treated reactors after shock also. These results showed that benzoate was able to prevent the "classical" shock response from phenol. The demonstration that benzoate feed concurrent with phenol feed gave complete protection suggests that the adaptation that occurs in the population is very rapid.

The reactor which received catechol behaved differently from that receiving the benzoate. Although perhaps not as effective as benzoate, the catechol was clearly more effective than no treatment.

TABLE 1

CSTR RESPONSE TO PHENOL SHOCK LOADING (REACTOR PHENOL LEVELS IN PPM)

| Hours | Control | 25 ppm Benzoate | 25 ppm Benzoate at Shock | 12.5 ppm Catechol/ 12.5 ppm Benzoate | 25 ppm Catechol |
|---|---|---|---|---|---|
| 0 | 0.00 | 0 | 0 | 0.00 | 0.00 |
| 3 | 17.79 | 0 | 0 | 10.02 | 25.74 |
| 23 | 74.72 | 0 | 0 | 0.50 | 54.38 |
| 46 | 94.77 | 0 | 0 | 0.38 | 83.15 |
| 70 | 110.29 | 0 | 0 | 0.52 | 100.96 |

TABLE 2

CSTR COD LEVELS (PPM) BEFORE, DURING AND AFTER PHENOL SHOCK LOADING; W/ & W/O ANALOG EXPOSURE

| Days | 25 ppm Benzoate | 25 ppm Catechol | Control | 25 ppm Benzoate at Shock | 12.5 ppm Catechol/ 12.5 ppm Benzoate |
|---|---|---|---|---|---|
| −4 | 292 | 356 | 410 | 471 | 279 |
| −1 | 251 | 244 | 422 | 416 | 279 |
| 0 | 251 | 279 | 393 | 404 | 222 |
| 1 | 299 | 331 | 560 | 485 | 279 |
| 2 | 325 | 433 | 680 | 433 | 324 |
| 3 | 293 | 569 | 1,004 | 497 | 356 |

The system which received catechol alone prior to phenol shock showed phenol breakthrough similar to, but not as extreme as the control reactor, indicating that only minor prevention of that effect occurred. The system which received a mixture of benzoate and catechol had a slight breakthrough of phenol and a rapid return to baseline, indicating that as little as 12.5 ppm benzoate was able to substantially mitigate the effects of the phenol shock.

It appeared from these findings that benzoate offered the protection from phenol shock loading that was expected. However, the rapidity of the response that occurred when benzoate was fed concurrently with the shock was unexpected. Another experiment was conducted to confirm that benzoate was able to prevent shock loading effects, to demonstrate what dose-related responses could be seen, and to investigate how far into the phenol shock benzoate could be applied and still be effective.

Figure 3:
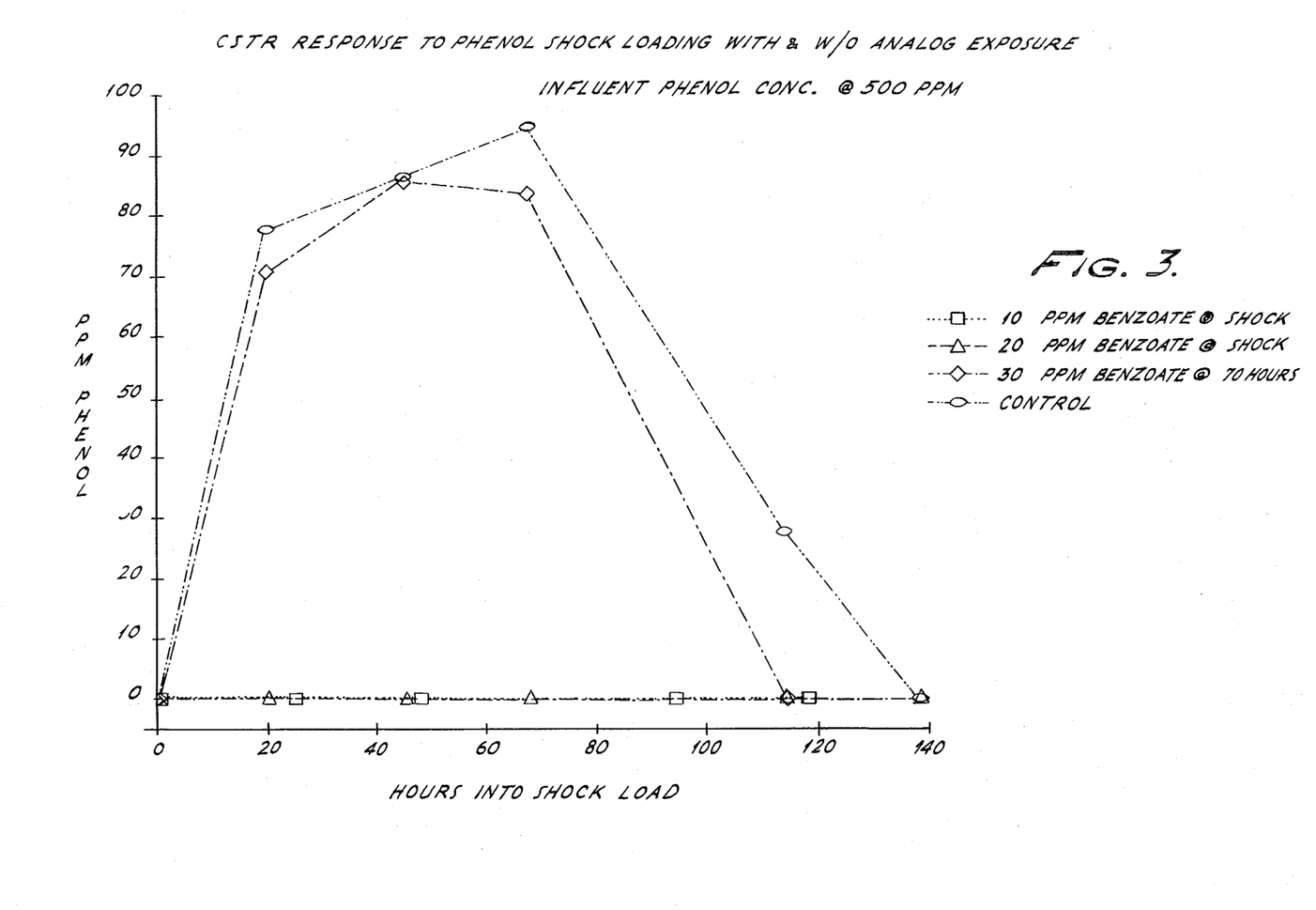
Figure 4:
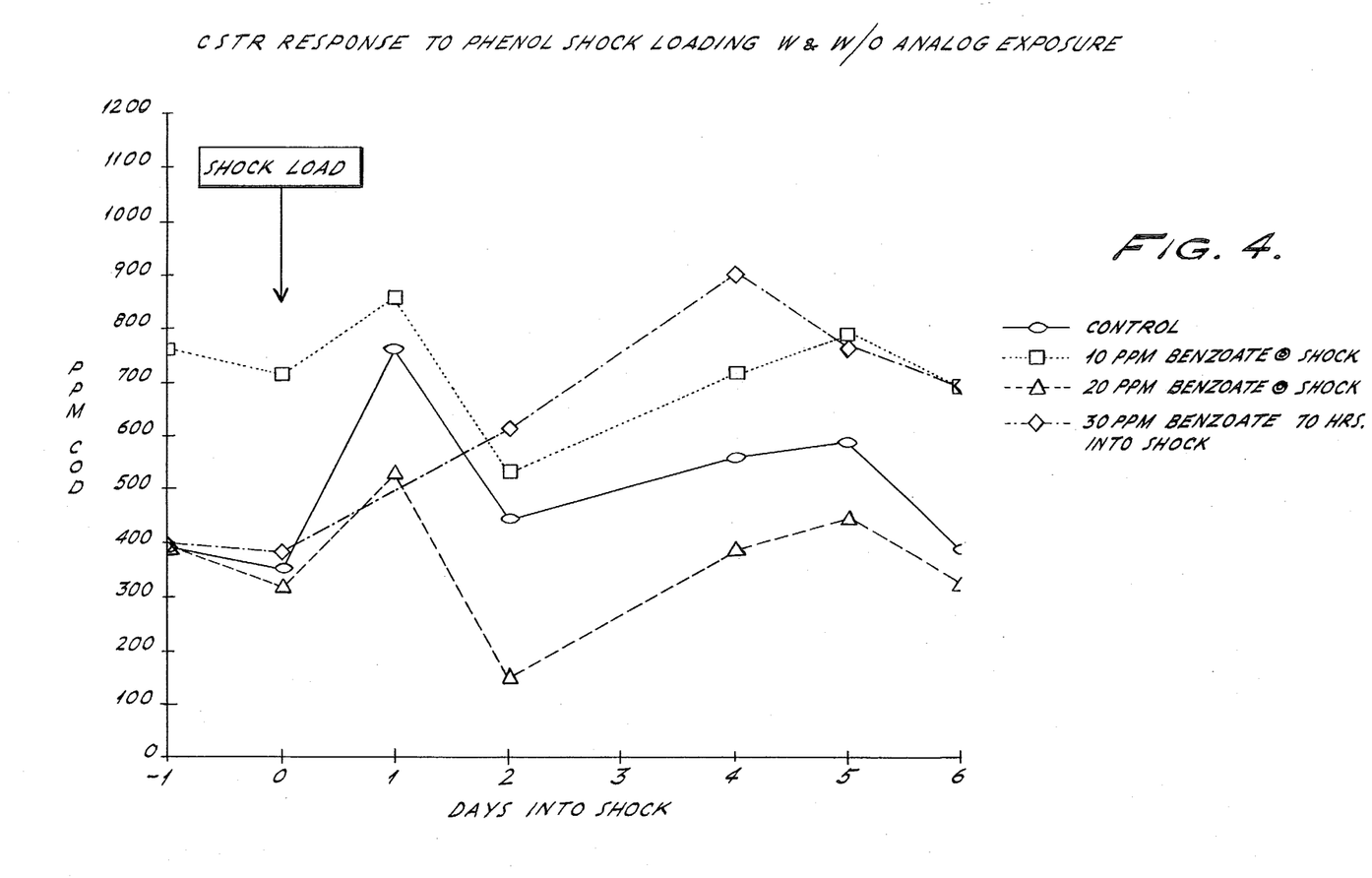

FIGS. 3 and 4 and Tables 3 and 4 show phenol and COD levels of CSTRs subjected to phenol shock loading at 500 ppm under the following modes of operation:
(A & B) 10 & 20 ppm benzoate, respectively, begun at phenol shock load inception and fed continuously throughout the shock load;
(C) 30 ppm benzoate added 70 hours into the shock load to determine whether recovery time would improve;
(D) control which received no benzoate.

All other reactor operating parameters were the same as those utilized in the initial laboratory study.

Results from this series of experiments in the control reactor showed the complete course of a phenol shock load, from inception, to peaking out of phenol breakthrough (up to 94.6 ppm phenol) to complete "die off" of the compound and system recovery. COD assays showed slight inhibition of COD removal but rapid recovery in the control. The reactors treated with 10 and 20 ppm of benzoate showed no phenol breakthrough at all, indicating that a minimal amount of analog is necessary to completely protect the population from phenol shock.

On the other hand, 30 ppm benzoate added after the shock load had progressed for 70 hours showed apparently accelerated recovery from phenol shock.

COD levels of the reactors dosed with benzoate at shock inception did not show the stability of the previous run where analogs were fed continuously prior to shocking. All reactors showed some oscillation with regard to organic removal efficiency, and interpretations are clouded. The only clearly repeated pattern of COD response was shown by the reactor dosed after shock began.

The data showed that sodium benzoate did prepare the mixed culture population for phenol degradation, when fed prior to exposure to phenol, concurrently with exposure to phenol, and possibly even after exposure to phenol. Catechol, in contrast, does not vastly improve the response of this particular population to phenol. However, the results of this preliminary test do not mean that it can be concluded that catechol would not be effective with other microbial populations which might be more susceptible to and adapted by it.

TABLE 3

CSTR RESPONSE TO PHENOL SHOCK LOADING
(REACTOR PHENOL LEVELS IN PPM)

| Hours | Control | 10 ppm Benzoate at Shock | 20 ppm Benzoate at Shock | 30 ppm Benzoate 70 Hours into Shock |
|---|---|---|---|---|
| 0.0 | 0.00 | 0 | 0 | 0.00 |
| 20.0 | 77.70 | 0 | 0 | 70.60 |
| 25.0 | | 0 | 0 | |
| 45.0 | 86.32 | | | 85.70 |
| 47.5 | | 0 | 0 | |
| 67.5 | 94.57 | 0 | 0 | 83.58 |
| 94.0 | | | | |
| 114.0 | 27.41 | | | 0.00 |
| 118.0 | | | | |
| 138.0 | 0.00 | | | |

Influent phenol level at 500 ppm.

The laboratory data concerning dosing suggested that phenol analogs could be applied either on a continuous or semicontinuous basis before the shock load occurs, or after the shock load has begun, or analog could be added into wastewater storage vessels and thereby added to the aeration basin when wastewater is purged in.

The reproducibility of COD removal data between the two runs was poor, and reasons for this are unknown. However, in all instances the benzoate treatment did not appear to adversely affect COD removal, so the lack of reproducilibty was not of great concern.

TABLE 4

CSTR COD LEVELS (PPM) BEFORE,
DURING AND AFTER PHENOL SHOCK LOADING;
W/ & W/O ANALOG EXPOSURE

| Days | Control | 10 ppm Benzoate at Shock | 20 ppm Benzoate at Shock | 30 ppm Benzoate 70 Hours into Shock |
|---|---|---|---|---|
| −1 | 393 | 761 | 397 | 398 |
| 0 | 353 | 713 | 321 | 384 |
| 1 | 762 | 855 | 530 | |
| 2 | 444 | 530 | 150 | 612 |
| 4 | 558 | 713 | 384 | 899 |
| 5 | 585 | 786 | 444 | 762 |
| 6 | 384 | 688 | 321 | 688 |

Pilot Scale Testing

To study the invention in a larger and perhaps more relevant environment, a pilot scale test was conducted at a midwest refinery which was experiencing some difficulty in meeting its discharge limitations for phenols. The refinery's predicament with phenol treatment was seasonal, and appeared perfectly amenable to an analog-type solution. Gasoline storage tanks laden with phenol were a problem in the wet season (Spring, Fall, and Winter). Rain or snow melt accumulated in these tanks, as did caustic phenol. Eventually a release of phenol water had to be made or another storage vessel annexed. Either way, disposal of phenolic wastes was necessary. Despite calculated additions of this segregated waste to their treatment system to prevent phenol breakthrough, shock loads frequently occurred in the biological operations. Added aggravation came about to plant operations when this situation contributed to overloading of refinery desalters. Phenol concentrations of up to 10,000 ppm had been generated in the storage water thereby creating shock load problems which resulted at least in one instance in the destruction of the biological activity in the refinery waste treatment system.

A specialty chemical solution had great appeal to the refinery's environmental operations personnel especially if it could solve their problem with minimum capital investment. Accordingly, a study was made of a sidestream reactor comprised of a parallel bioreactor system, using the refinery wastewater and phenol source as influent substrates, and a microbial population collected from the phenol waste treatment system.

Procedure and Equipment for Pilot Scale Testing

The bioreactor was designed to mimic the laboratory model used in the previous studies. The primary substrate feed was split into the two reactors and the secondary substrate, with and without the analog, was fed from a separate reservoir. The ratio between primary and secondary feedrates was similar to the laboratory study ratio. The differences of the field reactor setup from the laboratory setup were significant, however. There was no attempt to control the pH of the reactors; the primary substrate feed was fresh effluent from the IAF and thus was uncharacterized and not constant, but it contained some phenol; the secondary substrate was phenol wastes from the storage tank, which was also uncharacterized and not pure; the seed for the bioreactor was derived from the primary oxidation pond and the biofilm of the rotating biological contactor.

Reactors for aeration lagoon modeling were constructed from high density polyethylene cylindrical tanks with a 30 gallon capacity and 100 liter working volume (18 in. I.D.×30 in. depth). Tanks were fitted with four evenly spaced 2 in.×28 in. polyethylene baffle, a quad-headed aeration manifold constructed from ½" PVC tubing fitted to the reactor bottom, and a variable speed (0-1750 rpm) Lightnin mixer. The agitation system was completed with a 24" stainless steel shaft and a flat blade (2 in. dia., 3 bladed) turbine impeller. The agitation system was fitted into the reactor cover. Mixing settings were 55/100 or 960 rpm.

Air delivery was made with a dual-headed air pump at a flow rate of 1100 cu. in./min. per channel.

Substrate delivery was executed in a fashion similar to the lab setup through the use of a segregated pumping system for primary (IAF effluent) and secondary (phenol water and analog if used) substrates. Pumps used were multiple head pumps.

Primary substrate was pumped from a hold tank, which was filled by refinery personnel, three times daily, with refinery IAF unit effluent. Phenol water source for shock loading was from refinery storage tanks. Benzoate was added to the phenol water in the secondary reservoir, and the final concentration of benzoate in the reactor was 25 ppm.

Reactor startup was begun by overnight aeration and agitation of 80 liters of 1:4 dilution of IAF effluent, followed by seeding with 20 liters of #1 pond mixed liquor and 200 mL of a 1:2 dilution of biodisc #1 biofilm the following day. Batch operation ensued for 3 days and then continuous culture was instituted at a dilution rate of 0.010 hr$^{-1}$, or a hydraulic retention time (HRT) of 4.2 days (the reported HRT of the full scale system). Reactors were run for 11 days before the shock load was begun, but benzoate was fed to one reactor continuously beginning on day 7, thus, the treatment preceded shock inception by 4 days. Phenol shock ran for 5 days, at which time phenol levels had returned to baseline.

The analytical procedure for measuring COD was the same in the field and laboratory studies. However, phenol analyses were not performed with capillary gas chromatography, as in the laboratory studies, but rather with a Chemetrics field test kit. This test kit is incapable of measuring many phenolics, but does measure some besides phenol. Thus the analyses for "phenol" have some room for interpretation. However, the results were repeatable, the tests worked well in the field, and the same test procedure was used by plant personnel to monitor phenol levels. All samples were run on soluble fractions filtered through Amicon 25 mm, 0.45 μm microporous filters (cell densities interfered with low level phenol analysis).

Observations

Figure 5:
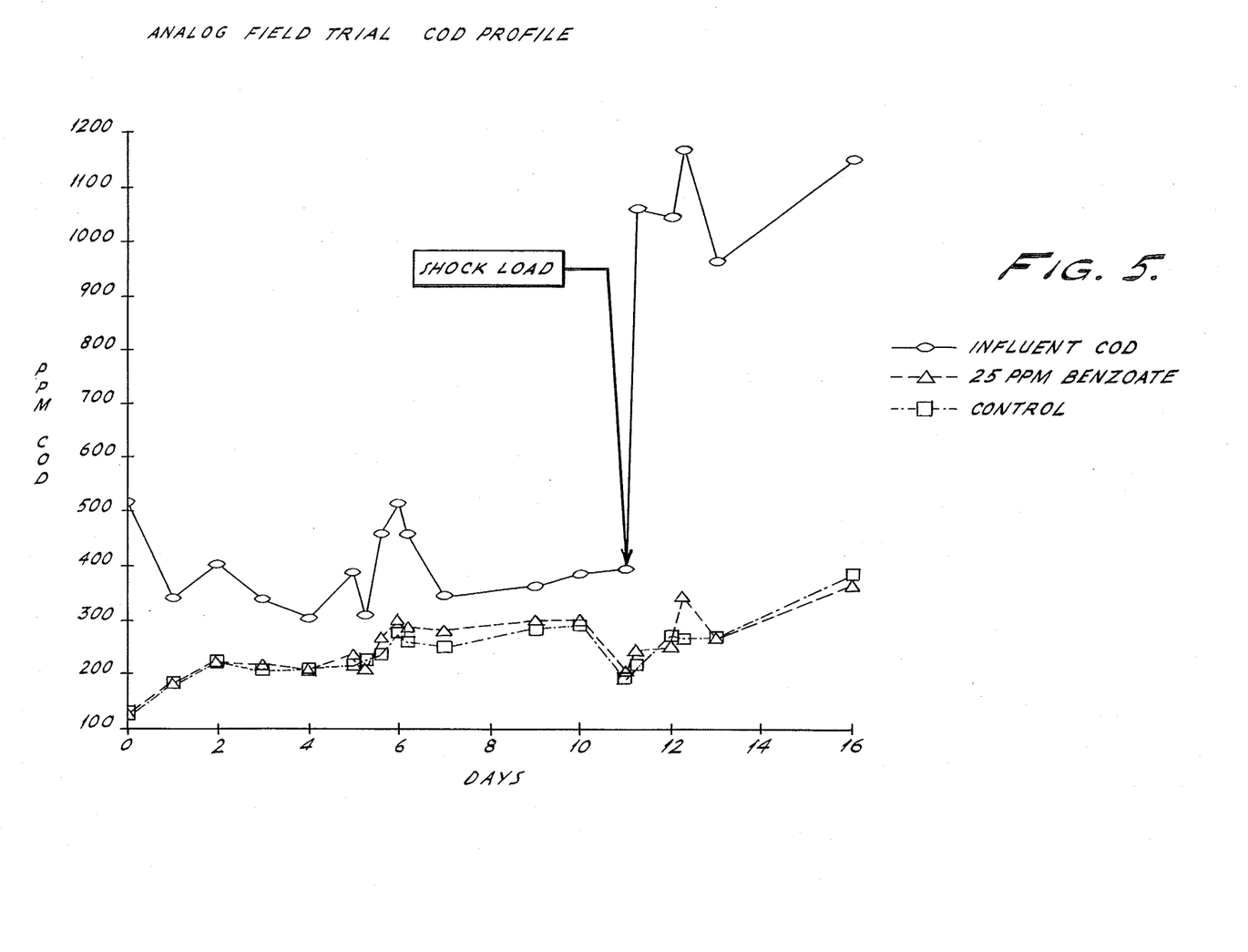
Figure 6:
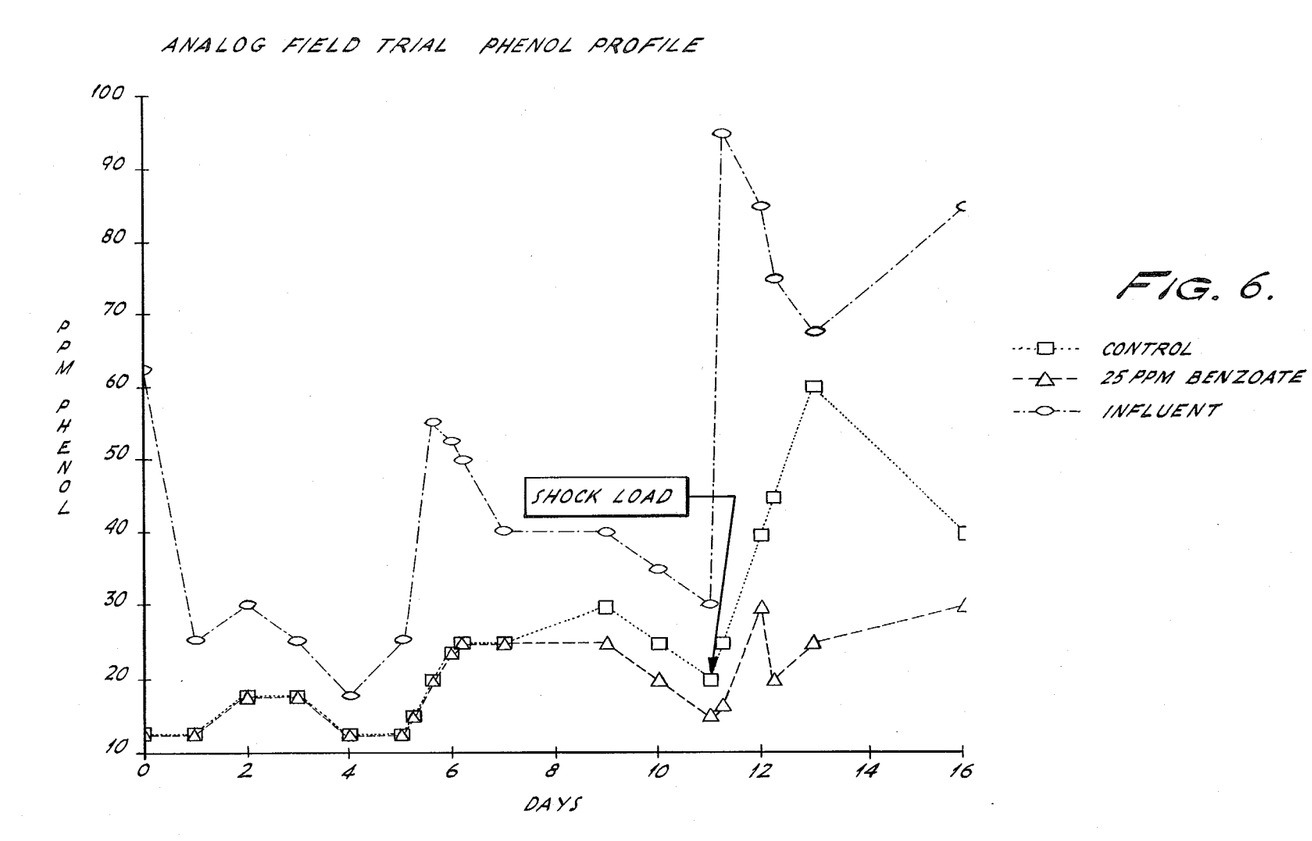

The data from the trial are shown in Table 5 and FIGS. 5 and 6. The pH remained reasonably stable in both reactors, despite considerable fluctuation in pH of the primary substrate and absence of pH control. The data showed that the reactors paralleled one another throughout the run, even after benzoate treatment and phenol shocking.

The results of COD measurements on the influent to the reactors and the effluent from the reactors are shown in FIG. 5. While the COD loading on the reactors increased more than twofold after the phenol shock began, no difference in COD removal between the reactors was evident after shocking.

The COD removal profiles demonstrate the excellent parallel performance of the two reactors. The COD level of the influent (IAF effluent) varied prior to phenol shocking, and increased markedly after shock loading began. The effluent from the reactors showed similar COD levels, indicating similar COD removal efficiencies.

The inability of the pilot scale treatment systems to remove greater than 95% of the COD, a typical removal efficiency, can probably be attributed to two effects. The first, and probably minor, is influence exerted by the low temperature of the reactors which slows bioactivity. The more important factor was most likely that the solids retention time (SRT) was too short. Preliminary discussions with refinery personnel about their treatment system indicated that the SRT was 3-5 days. An SRT of 4.2 days was chosen for the bioreactors to mimic this residence time and dilution rate. Later in the trial it was determined that the real SRT of the fullscale system was more on the order of 11-14 days. If this residence time had been used in the model reactors it is likely that a larger degree of COD removal would have been achieved.

Phenol removal efficiency of both reactors was also equivalent prior to the introduction of the analog benzoate to one reactor on day 7. Effluent phenol levels mirrored the influent levels up to day 7. The influent level increased dramatically on day 11 due to the inception of the phenol shock. The effluent of the control reactor had increased phenol concentrations through day 13, then decreased, which was a typical, expected shock load response in a system in which the shock load does not exceed the toxic dose. If the shock had been toxic, both COD and phenol levels in the effluent would have increased to the levels found in the influent. The phenol concentrations in the effluent from the benzoate treated reactor differed significantly from those in the control. It was evident that even before shock loading began, on days 9 through 11, phenol removal was improved in the reactor which received the analog. After shock loading began on day. 11, the benzoate-treated reactor had much lower phenol levels in the effluent than the control did. On day 13, only 11% of the phenol entering the control reactor was removed while the analog-treated reactor removed 63% of the phenol. It is assumed that, had the residence time in the reactors been lengthened, the degrees of phenol removal would have been higher.

TABLE 5

ANALOG FIELD TRIAL

| Days | Temp (C.) | IAF pH | IAF Phenol (ppm) | IAF COD (ppm) | Control pH | Control Phenol (ppm) | Control COD (ppm) | 25 ppm Benzoate pH | 25 ppm Benzoate Phenol (ppm) | 25 ppm Benzoate COD (ppm) | Influent Phenol (ppm) | Influent COD (ppm) |
|---|---|---|---|---|---|---|---|---|---|---|---|---|
| 0.00 | 11.0 | 8.78 | 62.5 | 520 | 8.23 | 12.5 | 132 | 8.27 | 12.5 | 125 | 62.5 | 520 |
| 1.00 | 11.0 | 8.68 | 25.0 | 343 | 8.20 | 12.5 | 185 | 8.24 | 12.5 | 183 | 25.0 | 343 |
| 2.00 | 9.0 | 8.94 | 30.0 | 405 | 8.21 | 17.5 | 225 | 8.24 | 17.5 | 218 | 30.0 | 405 |
| 3.00 | 9.0 | 8.69 | 25.0 | 338 | 8.32 | 17.5 | 210 | 8.29 | 17.5 | 220 | 25.0 | 338 |
| 4.00 | 8.0 | 8.26 | 17.5 | 305 | 8.25 | 12.5 | 212 | 8.55 | 12.5 | 211 | 17.5 | 305 |
| 5.00 | 8.0 | 8.69 | 25.0 | 390 | 8.24 | 12.5 | 220 | 8.23 | 12.5 | 237 | 25.0 | 390 |
| 5.25 | | 8.71 | 30.0 | 310 | 8.31 | 15.0 | 228 | 8.31 | 15.0 | 208 | 30.0 | 310 |
| 5.60 | 10.0 | 8.81 | 55.0 | 460 | 8.25 | 20.0 | 237 | 8.26 | 20.0 | 268 | 55.0 | 460 |

TABLE 5-continued
ANALOG FIELD TRIAL

| Days | Temp (C.) | IAF pH | IAF Phenol (ppm) | IAF COD (ppm) | Control pH | Control Phenol (ppm) | Control COD (ppm) | 25 ppm Benzoate pH | 25 ppm Benzoate Phenol (ppm) | 25 ppm Benzoate COD (ppm) | Influent Phenol (ppm) | Influent COD (ppm) |
|---|---|---|---|---|---|---|---|---|---|---|---|---|
| 6.00 | 10.0 | 8.81 | 52.5 | 515 | 8.28 | 23.8 | 277 | 8.29 | 23.8 | 300 | 52.5 | 515 |
| 6.20 | 11.0 | 9.05 | 50.0 | 458 | 8.35 | 25.0 | 261 | 8.27 | 25.0 | 287 | 50.0 | 458 |
| 7.00 | 11.0 | 8.90 | 40.0 | 345 | 8.30 | 25.0 | 250 | 8.27 | 25.0 | 280 | 40.0 | 345 |
| 9.00 | 11.0 | 8.29 | 40.0 | 365 | 8.24 | 30.0 | 287 | 8.16 | 25.0 | 300 | 40.0 | 365 |
| 10.00 | 17.0 | 8.76 | 35.0 | 388 | 8.31 | 25.0 | 294 | 8.21 | 20.0 | 302 | 35.0 | 388 |
| 11.00 | 15.0 | 8.38 | 30.0 | 395 | 8.22 | 20.0 | 196 | 8.18 | 15.0 | 208 | 30.0 | 395 |
| 11.25 | 15.0 | 8.87 | 45.0 | 545 | 8.32 | 25.0 | 220 | 8.26 | 16.5 | 244 | 95.0 | 1,060 |
| 12.00 | 14.0 | 8.56 | 35.0 | 528 | 8.35 | 40.0 | 272 | 8.30 | 30.0 | 252 | 85.0 | 1,043 |
| 12.25 |  | 8.67 | 25.0 | 653 | 8.36 | 45.0 | 268 | 8.33 | 20.0 | 345 | 75.0 | 1,168 |
| 13.00 | 11.1 | 8.65 | 17.5 | 448 | 8.36 | 60.0 | 270 | 8.40 | 25.0 | 270 | 67.5 | 963 |
| 16.00 | 12.0 | 8.75 | 35.0 | 635 | 8.28 | 40.0 | 384 | 8.27 | 30.0 | 366 | 85.0 | 1,150 |

FIG. 6 is a representation of the data from phenol analyses on the reactor influent and contents. Benzoate feeding to one reactor began on day 7, and phenol shock began on day 11. It appears that 25 ppm benzoate improved phenol removal somewhat before shocking began. After the phenol shock was initiated, the phenol content of the control reactor rose markedly over a two-day period, then decreased toward baseline, a typical shock load response. The pattern was strikingly different with the benzoate-treated reactor. It is evident that the phenol levels therein remained much lower than the control reactor levels, indicating improved ability to degrade the phenol.

While some aspects of the reactor trial were less than ideal, the analog concept was largely supported by the pilot scale testing. Improved phenol removal occurred, and no disturbance of reactor performance was seen, following addition of benzoate to the reactor.

Field Application Trial

Because of the successes achieved at the refinery during the Pilot Scale Testing, a full trial was conducted over a two week period. The trial had as its goal the prevention of wastewater system failure due to phenol shock loading and the accelerated removal of phenols during such shock loading.

The trial was conducted utilizing the refinery's wastewater system.

Background/General Information

According to the configuration of the refinery's wastewater treatment system, wastewater from the refinery passed through an induced air flotation (IAF) unit and was deposited into the No. 1 Pond. All of the biological activity in the wastewater treatment system took place in the No. 1 Pond and rotating biological contactors (RBC). Aeration was provided via three separate aerators. Phosphoric acid was fed to increase the phosphorus concentration when it was determined that the level was too low. The outfall of No. 1 Pond was directed to two banks of RBC to further reduce phenol, BOD, etc., before being discharged to Pond No. 2. Ponds 2, 3, and 4 were serially-connected equalization basins which received the wastewater prior to discharge to a canal. Little biological reduction occurred in these ponds. The refinery monitored phenols at the IAF discharge and the influent/effluent of the RBC as well as the final effluent to the canal. During the course of the trial, phenol concentrations independently measured by refinery and trial personnel showed very close correlation.

Figure 7:
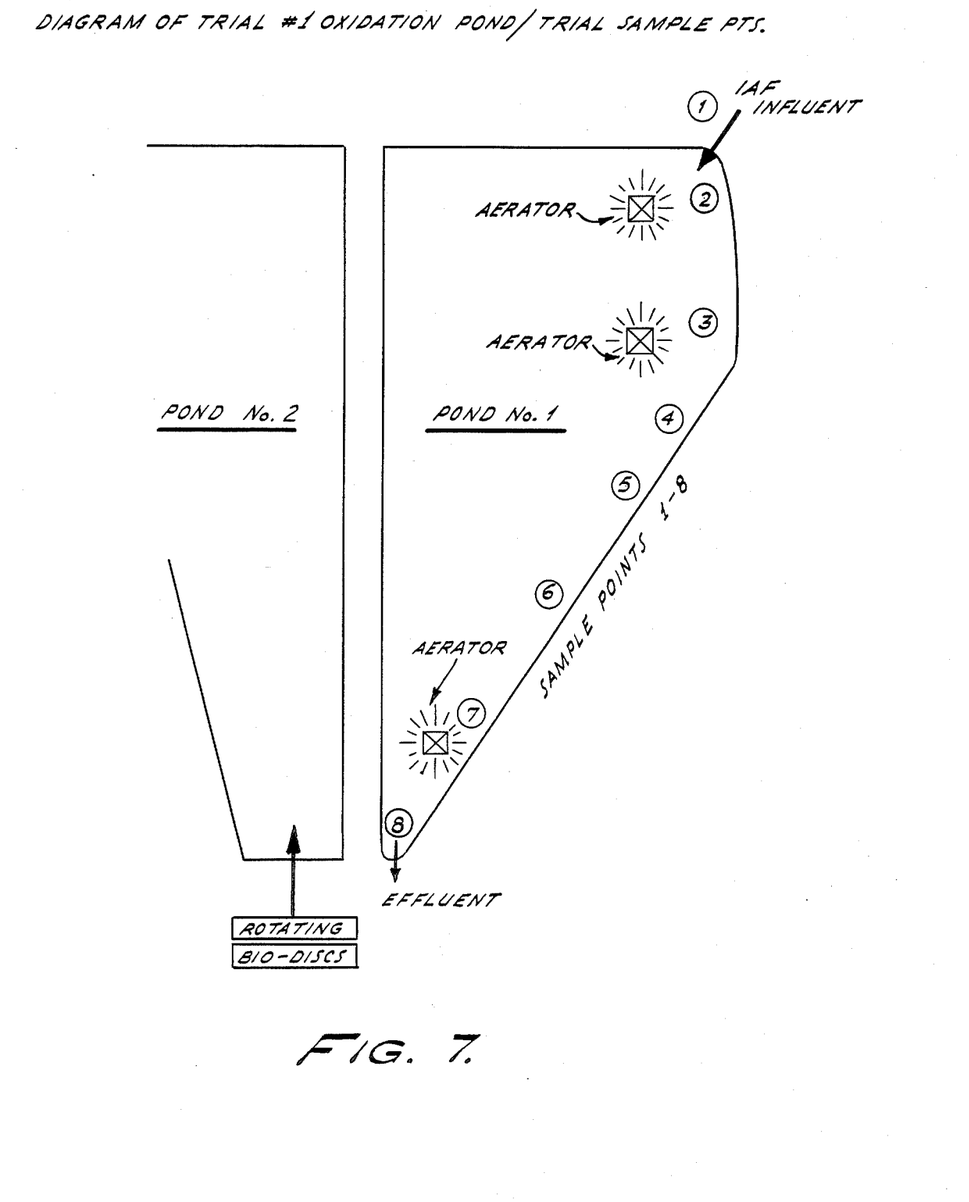

Based on numbers provided by the refinery, or directly measured by the trial personnel, the No. 1 Pond volume was determined to be $13 \times 10^6$ gallons, based on an average depth of 5 feet. The No. 1 Pond influent (IAF effluent) provided 700-900 gpm and, therefore, a dilution rate of 0.088 day$^{-1}$, based on an average flow rate of 800 gpm. This equated to a theoretical solids retention time (SRT) of 11 days if the system were uniformly mixed. Prior work had established a short-circuiting of the flow around the aerators (east side of pond) from the NE→SE ends of the pond, shortening the SRT to 2-3 days in this channeled area. Phenol measurements during this trial were concentrated in this channeled zone. A diagram of the No. 1 pond is shown in FIG. 7.

Phenolics are a natural result of the refining process and end up being discharged as waste at a relatively constant level. However, phenolics also end up in standing tanks of refined fuels in the tank farm. The tank farm units have floating lids which allow rain/snow melt to penetrate, and phenolics concentrate in the tank bottoms, which must eventually be drained off as the volume increases. Phenolics can become >10,000 ppm in these tank bottoms. When the tanks become full, the situation worsens and the phenolics must be drained to the No. 1 Pond at shock levels. Until this condition exists, phenolics could be drained to No. 1 Pond at controlled rates, which was an ongoing process. The normal phenol concentration to No. 1 Pond via IAF effluent, including tank farm contribution, was 30 ppm. Phenol shocks could be intentionally induced by increasing the tank farm contribution.

Field Trial Rationale

Ideally, a waste treatment facility with parallel units would be the preferred method for testing benzoate enhancement, thereby providing reasonable side-by-side control/benzoate-treated systems. In reality, few (if any) of these systems exist. Therefore, a site was selected where phenolics were a problem, where historical data on the waste treatment pond were available, and on which some control could be effected. Historical data provided by refinery personnel indicated that the system had previously failed when 60 ppm phenol entered No. 1 Pond via the IAF for brief periods of time. Breakthrough of phenol to the RBC was not tolerable and 2-3 ppm phenol breakthrough to the RBC had been catastrophic by past experience. When the No. 1 Pond system was "dead", breakthrough to the RBC occurred with only 10-20 ppm phenol entering the pond via the IAF. Performance of benzoate could be judged based on movement of a shock phenol 'wave' through the channeled area of the No. 1 Pond and on the ability of the acclimated microbial population to remove the phenol shock.

The wastewater system was monitored for phenol concentration, COD content, pH, and temperature for several days prior to the introduction of benzoate. Of particular importance were the sampling points shown in FIG. 7, which were jointly established by trial and refinery personnel. These were concentrated on the east side of the pond. These areas had the highest phenol concentrations during a shock load and detection of phenol would be noted at these sampling points early in the shock condition. A phenol profile prior to benzoate addition was generated at a time when the phenol loading on the No. 1 Pond was at a normal level (25–30 ppm at influent). Benzoate feed was initiated after the third daily sampling of the No. 1 Pond, and was fed at a continuous rate of 13 ppm based on the No. 1 influent. Benzoate was fed via a 200-gallon tank/explosion-proof pump setup at the IAF unit and the feed was directed to the IAF effluent pipe which discharged directly to the No. 1 Pond. A continuous dosage regimen was chosen for several reasons. Since this was an initial field trial, and the amount of benzoate needed to 'condition' a virgin field population was unknown (necessary conditioning time frame was also unknown), it was felt that a stepwise conditioning scheme predating the anticipated shocks by 24–48 hours would give a sufficient safety interval in which we could work and react. The parameters noted in Table 6 were monitored for several days to determine the effects on the No. 1 Pond's handling of the influent phenol concentration and to condition the native microbial population to accept a planned phenol shock. The benzoate concentration was increased twice during the period just prior to the scheduled phenol shock (13 ppm→20 ppm→23 ppm) to further acclimate the resident microbes. The scheduled phenol shock occurred (lasting 17 hours) and the various parameters were measured prior to, during, and after the phenol shock.

RESULTS

Table 6 provides the phenol concentration data generated during the course of this trial. During the opening day, control samples were taken while no benzoate was being fed. The incoming phenol concentration was between 25–40 ppm from the IAF with immediate dilution of the phenol at the first pond sample point, No. 2. From there, dilution and microbial breakdown decreased the amount detected to a background level of 1.0 to 1.5 ppm of the remaining sample points along the pond. Differences were noted in the phenol analysis kits being used by trial/refinery personnel only at the lower detectable limits. Excellent correlation was obtained on phenol levels <2 ppm. Both were Chemets systems; however, the spectrophotometric method used by trial personnel was able to detect sub-ppm levels while the color comparator method used by the refinery made readings of <1 ppm very difficult. One ppm levels in the color comparator system did show visible pink color formation, making it a good yes/no test at these lower levels.

Since no background level greater than 1.5 ppm was noted at sample position 4, it was used as a benchmark to determine whether phenol levels >1.5–2 ppm would pass beyond that point. There was probably less than a one-day residence time between sample points 2 and 4.

TABLE 6

PHENOL PROFILE

| | DATE/TIME Phenol Conc. in ppm | | | | | | | | | |
|---|---|---|---|---|---|---|---|---|---|---|
| | 11/13 | | 11/14 | | 11/15 | | 11/6* | | 11/17 | 11/18 |
| SAMPLE AREA | 10 AM | 2 PM | 10 AM | 2:30 AM | 10 AM | 2 PM | 10 AM | 3 PM | 10 AM | 10 AM |
| 1. IAF Effluent | 14.0 | 27.2 | 38.0 | 36.8 | 46.0 | 40.0 | 12.0 | 12.0 | 30.0 | 27.0 |
| 2 | 1.4 | 11.3 | 6.3 | 5.3 | 7.0 | 5.4 | 1.6 | 1.0 | 3.8 | 2.0 |
| 3 | 1.5 | 1.4 | 5.0 | 1.5 | 4.5 | 2.4 | 1.2 | 0.5 | 1.7 | 1.2 (0.0) |
| 4 | 1.3 | 1.4 | 1.5 | 1.5 | 1.6 | 1.4 | 0.5 | 0.5 | 1.0 (0.1) | 0.5 |
| 5 | 1.3 | 1.4 | 1.3 | 1.3 | 1.4 (0.2) | 1.2 | 0.5 | 0.5 | 0.5 | 0.5 |
| 6 | 1.2 | 1.4 | 1.0 | 1.3 | 1.4 | 1.2 (0.2) | 0.5 | 0.5 | 0.5 | 0.5 |
| 7 | 1.2 | 1.2 | 1.2 | 1.3 (0.2) | 1.4 | 1.2 | 0.5 | 0.5 | 0.5 | 0.5 |
| 8 | 1.0 | 1.2 | 1.2 | 1.2 (0.2) | 1.4 (0.1) | 1.0 (0.1) | 0.5 | 0.5 (0.0) | 0.5 | 0.5 |

FEED BEGUN 11/14/84 10:15 AM

| | DATE/TIME Phenol Conc. in ppm | | | | | | | | | | |
|---|---|---|---|---|---|---|---|---|---|---|---|
| | 11/19/84 | | | | | | | 11/20/84 | | | |
| SAMPLE AREA | 9 AM | 11:30 AM | 12:00 PM | 1:30 PM | 3:30 PM | 7:00 PM | 8:00 PM | 12:00 AM | 5:00 AM | 8:00 AM | 2:00 PM |
| 1. IAF Effluent | 36.0 | 46.0 | 80.0 | 151.0 | 180.0 | 150.0 | 120 | 105 | 95 | 6.5 | 20.0 |
| 2 | 2.8 | 7.6 | | 18.3 | 24.0 | 30.2 | | | | 3.4 | 3.5 |
| 3 | 1.5 | 4.1 | | 16.0 | 25.0 | 21.5 | | | | 3.8 (2.0) | 2.0 |
| 4 | 0.5 (0.2) | 1.5 (0.0) | | 1.8 | 2.0 | 1.3 | | | | 3.5 | 2.0 |
| 5 | 0.5 (0.0) | — | | 1.4 (0.0) | 0.5 | 0.5 | | | | 3.0 (1.0) | 2.0 (0.5) |
| 6 | 0.5 | — | | 0.5 (0.0) | 0.5 (0.2) | 0.5 (0.0) | | | | 3.0 (1.0) | 1.5 |

TABLE 6-continued

PHENOL PROFILE

| | | | | | | | | | | |
|---|---|---|---|---|---|---|---|---|---|---|
| 7 | 0.5 | — | 0.5 | 0.5 | 0.5 | | | | 1.5 | 0.3 |
| | | | (0.0) | | | | | | (0.5) | (0.0) |
| 8 | 0.5 | 0.5 | 0.5 | 0.5 | 0.5 | 0.0 | 0.0 | 0.0 | 1.2 | 0.3 |
| | | (0.0) | (0.0) | (0.0) | (0.0) | | | | (0.0) | (0.0) |

( ) Chemet Type P-12 Color Comparator
*Friday - Tank Farm Phenol Contribution Shut Off for Weekend - Reestablished Late 11/16

Benzoate feed was initiated at 10:15 a.m. on day 2. Incoming phenol levels during day 2-3 were above normal (35-50 ppm) and yet the phenol level measured at positions 3 and 4 were lower than control samples, indicating some increased removal. In addition, refinery personnel were intentionally decreasing the volume of No. 1 pond in preparation for the planned phenol shock. This was done as a safety factor so that a shock wave of phenol passing down the pond (in case of benzoate failure) could be detected and the pond capped off to prevent discharge to the RBC. With the residence time thus lengthened, the phenol could be held until degraded or diluted. By decreasing the pond volume, but holding the flow rate (IAF effluent) constant, the No. 1 pond SRT was being significantly reduced. The 3-inch drop in the pond level decreased the SRT from a theoretical 11.4 days to 10.6 days or 7%. In an actual two-day SRT in the channeling area, the SRT would drop more than three hours, indicating that phenols should have shown up faster than ever at sample position 4 and beyond. However, in spite of increased incoming phenol levels and decreased SRT, the phenol levels at the benchmark position 4 remained the same or decreased after benzoate feed began.

On day four, the tank farm phenol contribution was eliminated as is standard operating procedure for the refinery on weekends; and the phenol levels were low. Upon consulting with the refinery engineers, the tank farm contribution was reestablished by the afternoon of day 4 and remained at the 25-30 ppm level over days 5 and 6, with extremely low levels of phenol being detected from sample points 3 through 8. A phenol shock of 75 ppm for 4 hours was planned for the morning of day 7.

Data relevant to the COD, temperature and pH analyses, respectively, during the trial were recorded. COD data revealed that the amount of oxidizable material that was available in both the IAF and No. 1 Pond was very low unless the system is in an upset condition. Visual observations and COD data confirmed that two serious oil upsets occurred during the benzoate trial, one unintentional (day 3) and one due (at least in part) to the oil/phenol shock (day 7). The day 3 upset was due to an IAF problem which dumped oily waste into the No. 1 Pond for at least 4-6 hours. Refinery personnel detected this upset in their daily oil/grease measurements. Since benzoate was fed to the IAF, benzoate was oil/grease tested and the refinery confirmed that benzoate was not contributing to the oil/grease problems. Phenol levels also rose in direct response to the upset, but were handled effectively. The COD dropped significantly at sample point 2, which indicated the microbial population removed some of the oil, but the majority of the oily sludge was skimmed from the pond surface by refinery personnel. The day 7 upset was, in part, caused by the intentional shock loading of phenol to the system by means of the controlled dumping of the tank (farm) bottoms. Heavy hydrocarbon fouling of the No. 1 Pond occurred along with the phenol shock.

Temperatures of the No. 1 Pond sample areas held very steady during the course of the trial, eliminating this as a significant variable. The pH profile of the No. 1 Pond also held steady during the course of this trial except during the heavy phenol/oil shock on day 7.

The planned phenol shock took place on day 7. Weekend IAF effluent levels had been held steady at 25-30 ppm, while benzoate had been fed continuously at 23 ppm. Samples of the IAF effluent taken independently by trial and refinery personnel showed a rapid rise in the phenol concentration of from 35 ppm (10:00 a.m.) to 80 ppm (12:00 p.m.) to 150 ppm (1:30 p.m.). IAF effluent water quality deteriorated rapidly as the tank farm bottoms contribution increased. Turbidity and oil content increased significantly along with the phenol concentration. By 3:30 p.m., the phenol level was still rising (180 ppm) in the IAF, and did not drop below an influent concentration of 100 ppm until 5:00 a.m. on day 8. The shock duration was for 17 hours at well over 100 ppm, and at least as high as 180 ppm, which was 2-3× the phenol concentration and 4× the duration of the original shock regimen planned. After a short delay, the phenol concentration did, as expected, increase at various sample positions, but the phenol concentration at the benchmark position 4, remained only slightly above or at background (background being the concentration at any sample point during an IAF effluent level of 20-30 ppm). The expected phenol shock wave only occurred between positions 2 and 4 and did not extend beyond to any subsequent sample points until day 8, when some additional phenol was detected as far down as sample position 6. Using these phenol concentrations and times, it can be calculated that the SRT in the upper half of the No. 1 Pond can be no more than 12-15 hours, while the SRT in the lower half is more likely in the range of 45-48 hours. These are maximum SRT's, due to the fact that phenol would show up faster were it not being degraded rapidly by the microbial population on its way down the pond.

During the 17-hour course of the phenol shock, 820 pounds (average 120 ppm for 17 hours) of phenol were introduced via the IAF to No. 1 Pond. Considering the dimensions, SRT and channeling effects of the pond, dilution of this shock would theoretically produce a concentration of 30-40 ppm at the benchmark position 4. In reality, position 4 only had a concentration of 3-3.5 ppm, eight-ten hours after the shock (reconfirming the approximate SRT in that part of the pond). The microbial population must have been responsible for 85-90% of the phenol removal which took place in the No. 1 Pond by the time the benchmark position 4 was reached. The remaining part of the shock was reduced to background by the time sampling position No. 6 was reached. The phenol levels were again at background on day 8, indicating the shock had passed and the No. 1 Pond had withstood the shock. Benzoate feed was then reduced and the trial terminated.

At no time before, during or after the phenol shock did the phenol concentration in the lower half of the No. 1 Pond approach a level of concern, and a phenol breakthrough did not occur in spite of the magnitude of the phenol shock load.

Conclusions From the Full-Scale Trial

1. Benzoate treatment prevented phenol breakthrough and wastewater system failure of the refinery's No. 1 Pond during both elevated and shock level phenol doses.

2. The benzoate-conditioned microbial population handled phenol levels in excess of background levels readily. There were strong indications that microbial conditioning required less than 24 hours exposure to treatment.

3. Benzoate-conditioned populations showed accelerated phenol removal (phenol detected only at early sample points) in spite of simultaneous conditions of increased phenol influent concentration and decreased solid (hydraulic) retention time.

4. Intentional phenolics shock load of 820 pounds over 17 hours resulted in:
   a. no phenolics breakthrough from No. 1 Pond;
   b. no phenol "wave front" beyond No. 1 Pond midpoint; and
   c. greater than 90% phenol removal by conditioned microbial population by No. 1 Pond midpoint.

5. No. 1 Pond pH increase of 0.5 pH units did not alter the ability of the microbial population to degrade the phenol shock.

6. Severe oily sludge discharges (high COD loadings) to No. 1 Pond during phenol shocking did not affect product performance.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

We claim:

1. A method of improving the amount and rate of the biodegradation of an undesirable toxic aromatic organo compound to more acceptable, less toxic forms, which comprises under appropriate conditions, exposing in an aqueous medium said compound to a microbial population which is capable of biodegrading the said organo compound to said more acceptable form, the improvement being treating said microbial population with a sufficient amount for the purpose of a chemical which is structurally analogous to said compound, and which chemical, because of its analogous structure to the compound, permits the microbial population to adapt to the chemical and thereby affect the population in such a manner that its degradation capacity for said compound is increased without a substantial attendant increase in population.

2. A method according to claim 1 wherein the microbial population is exposed to said chemical concurrently with its exposure to said organo compound.

3. A method according to claim 2 wherein the concentration of compound subject to biodegradation fluctuates and the feed of the chemical used to treat said microbial population is continued during the fluctuations.

4. A method according to claim 3 wherein the concentration of chemical used increases with the amount of compound subjected to the microbial population.

5. A method according to claim 3 wherein the microbial population is treated with an increased amount of said chemical after the population has been exposed to an increased shock amount of said compound, thereby allowing said microbial population to recover from said shock.

6. A method according to claim 1, 2, 3, 4, or 5 wherein the biodegradation capacity of the microbial population is enhanced by its adapting to said chemical thereby stimulating the production of a greater supply of enzyme in the microbes of said population, which enzyme is required for the bioconversion of said compound.

7. A method of improving the amount and rate of the biodegradation of an undesirable toxic phenolic compound to more acceptable, less toxic forms, which comprises under appropriate conditions, exposing in an aqueous medium said compound to a microbial population which is capable of biodegrading the said phenolic compound to said more acceptable form, the improvement being treating said microbial population with a sufficient amount for the purpose of a benzoic acid derivative which is easily degraded by the population and which is structurally analogous to said phenolic compound, and which derivative, because of its analogous structure to the compound, permits the microbial population to adapt to the derivative and thereby affect the population in such a manner that its degradation capacity for said phenolic compound is increased without a substantial attendant increase in population.

8. A method according to claim 7 wherein the microbial population is exposed to said derivative concurrently with its exposure to said phenolic compound.

9. A method according to claim 8 wherein the concentration of the phenolic compound subject to biodegradation fluctuates and the feed of the derivative used to treat said microbial population is continued during the fluctuations.

10. A method according to claim 9 wherein the amount of derivative used increases with the concentration of phenolic compound subjected to the microbial population.

11. A method according to claim 9 wherein the microbial population is treated with an increased amount of said derivative after the population has been exposed to an increased shock amount of said phenolic compound thereby allowing the microbial population to recover from said shock.

12. A method according to claim 8 wherein the biodegradation capacity of the microbial population is enhanced by its adapting to said derivative, thereby stimulating the production of a greater supply of enzyme in the microbes of said population, which enzyme is required for the bioconversion of said compound.

13. A method according to claim 7, 8, 9, 10, 11, or 12 wherein the phenolic compound is phenol and the derivative is benzoic acid.

14. A method according to claim 13 wherein the biodegradation is taking place in a dynamic waste treatment system having a mixed microbial population.

* * * * *